United States Patent

Lantzsch

Patent Number: 5,304,651
Date of Patent: Apr. 19, 1994

[54] PROCESS FOR THE PREPARATION OF 5-SUBSTITUTED 2-CHLOROPYRIDINES

[75] Inventor: Reinhard Lantzsch, Wuppertal, Fed. Rep. of Germany

[73] Assignee: Bayer Aktiengesellschaft, Leverkusen, Fed. Rep. of Germany

[21] Appl. No.: 99,766

[22] Filed: Jul. 30, 1993

Related U.S. Application Data

[63] Continuation of Ser. No. 984,745, Dec. 3, 1992, abandoned.

[30] Foreign Application Priority Data

Dec. 13, 1991 [DE] Fed. Rep. of Germany ....... 4141188
May 22, 1992 [DE] Fed. Rep. of Germany ....... 4217021

[51] Int. Cl.$^5$ ............................................ C07D 213/08
[52] U.S. Cl. .................................................. 546/250
[58] Field of Search ........................................ 546/250

[56] References Cited

U.S. PATENT DOCUMENTS 4,504,664  3/1985  Nelson et al. .
5,010,201  4/1991  Kaufmann et al. .
5,099,025  3/1992  Kaufmann et al. .

FOREIGN PATENT DOCUMENTS 0108483  5/1984  European Pat. Off. .

OTHER PUBLICATIONS

115:158984b, Schnegg et al, "Preparation of 2-halopyridines", Chem. Abstr., V 115, (1991), p. 923.
Journal of the Chemical Society, Perkin Transactions 1 No. 6, 1984, Letchworth GB pp. 1173–1182, O. Meth-Cohn et al. "A versatile new synthesis of quinolines and related fused pyridines. Part 12. A general synthesis of 2-chloropyridines and 2-pyridones."

Primary Examiner—Marianne M. Cintins
Assistant Examiner—John Peabody
Attorney, Agent, or Firm—Sprung Horn Kramer & Woods

[57] ABSTRACT

A new process for the preparation of 5-substituted 2-chloropyridines of the general formula (I)

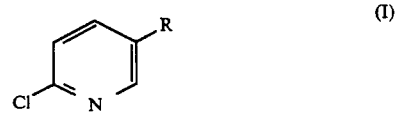

is provided, in which
R represents alkyl or arylalkyl, each of which is optionally substituted by halogen.

The new process is characterised in that acetenamides of the general formula (II)

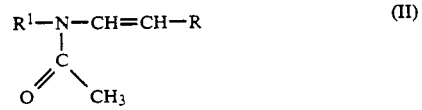

in which
R has the abovementioned meaning, and
$R^1$ represents alkyl or arylalkyl, each of which is optionally substituted by halogen, are reacted with a chlorinating agent in the presence of dimethylformamide and optionally in the presence of a diluent at temperatures between $-30°$ C. and $+150°$ C.

The compounds (I) prepared according to the invention may be used inter alia as intermediates for the preparation of highly efficient insecticides.

6 Claims, No Drawings

PROCESS FOR THE PREPARATION OF 5-SUBSTITUTED 2-CHLOROPYRIDINES

This application is a continuation, of application Ser. No. 984,745, filed Dec. 3, 1992, now abandoned.

The invention relates to a new process for the preparation of 5-substituted 2-chloro-pyridines.

It is known that 5-substituted 2-chloro-pyridines, such as, for example, 5-methyl-2-chloro-pyridine, are obtained when appropriate pyridine 1-oxides, such as e.g. 3-methylpyridine 1-oxide, are reacted with phosphoryl chloride (see EP-A 324174) or with other acid chlorides (see EP-A 438691 and EP-A 439745 and the prior art cited there).

However, the 5-substituted 2-chloro-pyridines produced in this way are always contaminated to a greater or lesser extent.

Furthermore, various multi-stage synthetic routes to 5-methyl-2-chloropyridine have been disclosed (see EP-A 108483, EP-A 121320 and EP-A 162464).

However, these syntheses are relatively costly and involve large losses.

It is furthermore known that mixtures of pyridones and pyridines are formed from certain enamides using phosphoryl chloride/dimethylformamide (see J. Chem. Soc. Perkin Trans. I 1984, 1173–1182). In this case, however, mainly pyridones are produced, while pyridines are only obtained as by-products.

It has now been found that 5-substituted 2-chloropyridines of the general formula (I)

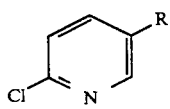

in which
R represents alkyl or arylalkyl, each of which is optionally substituted by halogen,
are obtained in a simple way in high yield if acetenamides of general formula (II)

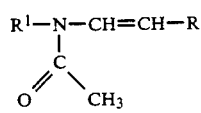

in which
R has the abovementioned meaning and
R¹ represents alkyl or arylalkyl, each of which is optionally substituted by halogen,
are reacted with a chlorinating agent in the presence of a N,N-disubstituted formamide e.g. dimethylformamide and optionally in the presence of a diluent at temperatures between −30° C. and +150° C.

In view of the prior art cited above (see J. Chem. Soc. Perkin Trans. I 1984, 1173–1182), it must be regarded as extremely surprising that the 5-substituted 2-chloropyridines of the formula (I) are obtained in high yield as the main products by the process according to the invention.

In contrast to the known processes mentioned above, the preparation of the starting materials of the formula (II) may take place starting from precursors which are commercially available on a large scale, isolation of the intermediate stages as pure substances not being required. The process according to the invention therefore represents a valuable extension of the prior art.

The course of the reaction in the process according to the invention may be outlined for example by the following reaction scheme:

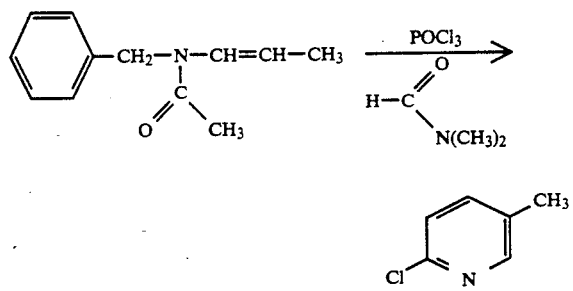

The process according to the invention preferably relates to the preparation of compounds of the formula (I) in which
R represents $C_1$-$C_6$-alkyl or phenyl-$C_1$-$C_2$-alkyl, each of which is optionally substituted by fluorine and/or chlorine.

In particular compounds of formula (I) in which
R represents methyl, ethyl or benzyl
are prepared by the process according to the invention.

The acetenamides to be used as starting materials are defined in general by the formula (II). In formula (II), preferably
R represents $C_1$-$C_6$-alkyl or phenyl-$C_1$-$C_2$-alkyl, each of which is optionally substituted by fluorine and/or chlorine, and
R¹ represents $C_1$-$C_4$-alkyl or benzyl, each of which is optionally substituted by fluorine and/or chlorine.

In particular, in formula (II),
R represents methyl, ethyl or benzyl and
R¹ represents benzyl.

The starting materials of the formula (II) are known and/or may be prepared by processes known per se (see J. Chem. Soc. Perkin Trans. I 1984, 1173–1182).

The acetenamides of the formula (II) are obtained for example when amines of the general formula (III)

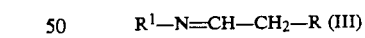

in which
R and R¹ have the abovementioned meaning
are reacted with acetic anhydride or acetyl chloride, optionally in the presence of an acid acceptor, such as, for example, triethylamine, and optionally in the presence of a diluent, such as, for example, toluene, at temperatures between 0° C. and 50° C. and worked up by conventional methods (see the preparation examples).

The imines of the formula (III) are known and/or may be prepared using processes known per se (see Chem. Abstracts 88:49759; preparation examples).

Chlorinating agents which may be used in the process according to the invention are compounds which form with formamides so-called Vilsmeier reagent, (N,N-disubstituted chloromethyl-immonium chloride (IV),

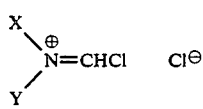

in which
X and Y represent $C_{1-4}$-alkyl or phenyl.

Formamides are dimethylformamide, dibutylformamide, phenyl-methylformamide, preferred is N,N-dimethylformamide.

This includes in particular acid chlorides, such as phosphoryl chloride (phosphorus oxychloride, $POCl_3$), phosphorus (V) chloride, phosgene, oxalyl chloride and thionyl chloride, but also organic polyhalogen compounds, such as perchlorobutanic-acidchloride and dichlorobenzodioxole. Phosphoryl chloride, oxalyl chloride and phosgene are especially preferred.

The process according to the invention for the preparation of the 5-substituted 2-chloro-pyridines of the formula (I) is optionally performed in the presence of a diluent. Virtually all organic solvents which are inert in the reaction may be considered. These preferably include aliphatic and aromatic, optionally halogenated, hydrocarbons such as hexane, heptane, cyclohexane, methyleyclohexane, benzene, toluene, xylene, chlorobenzene; o-dichlorobenzene, chloroform and totrachloromethane, and ethers such as methyl tort-butyl ether and 1,2-dimethoxyethane.

However, the use of an inert diluent is preferably dispensed with, i.e. the reaction is performed in excess N,N-disubstituted formamide as the diluent.

The reaction temperatures may be varied over a relatively wide range in the process according to the invention. The reaction is performed at temperatures between $-30°$ C. and $+150°$ C., preferably at temperatures between $-10°$ C. and $+130°$ C., especially at $0°$ C. to $20°$ C. in the first phase of reaction and then at $80°$ C. to $120°$ C.

The process according to the invention is performed in general under atmospheric pressure. However, it is also possible to work under reduced or elevated pressure between 0.1 bar and 10 bar.

To perform the process according to the invention, in general between 1 and 10 moles, preferably between 1.5 and 5 moles, especially between 2.0 and 3.0 moles of chlorinating agent and between 1 and 50 moles, preferably between 2 and 20 moles of dimethylformamide are used per mole of acetenamide of the formula (II).

In a preferred embodiment of the process according to the invention, the chlorinating agent and dimethylformamide are reacted first, preferably by initially introducing the dimethylformamide and adding the chlorinating agent to it slowly with slight cooling. The acetenamide of the formula (II) is then metered slowly into this mixture and the reaction mixture is stirred at elevated temperature until the end of the reaction.

Working-up may be performed in the normal way. For example, the mixture is diluted with ice water, extracted with an organic solvent which is virtually immiscible with water, such as methylene chloride, and the extraction solution is concentrated by evaporation. The product of the formula (I) may be obtained in pure form by vacuum distillation of the remaining residue.

The 5-substituted 2-chloro-pyridines to be prepared by the process according to the invention may be used as intermediates for insecticides (see EP-A 163855).

Preparation Examples

Example 1

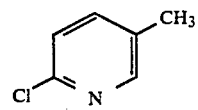

214 g (1.39 mol) of phosphorus oxychloride are added dropwise at an internal temperature of $5°$ C. to $10°$ C. to 565 ml (7.33 mol) of dimethylformamide over the course of 50 minutes. 113.7 g of N-benzyl-N-(1-propenyl)-acetamide (crude product from Example (II-1)) are then added dropwise at the same temperature. The reaction mixture is stirred for 16 hours at $100°$ C. and, after cooling, poured into about 1 litre of ice water. This is extracted four times with methylene chloride and the combined extraction solutions are evaporated.

112 g of a dark liquid are obtained which consists of 60.4% by weight of benzyl chloride and 35.7% by weight of 2-chloro-5-methylpyridine, according to gas chromatographic analysis.

This corresponds to a yield of 67.5% of theory over the last two stages (Examples (II-1) and 1).

After distilling twice, first under the vacuum provided by a water pump over a boiling range between $40°$ C. and $82°$ C. and then using an annular gap column (boiling point $118°$ C. at 60 mbar), pure 2-chloro-5-methyl-pyridine (97.3% pure) is obtained.

Example 2

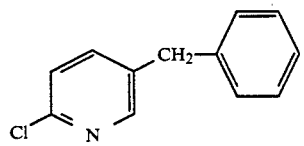

196 g (1.23 mol) of phosphorus oxychloride are added dropwise at $5°$ C. to $10°$ C. to 112 g (1.53 mol) of dimethylformamide over the course of 45 minutes. 137 g of N-benzyl-N-(3-phenyl-1-propenyl)-acetamide (crude product from Example (II-2)) are then added dropwise at the same temperature over the course of 30 minutes. The reaction mixture is stirred for 12 hours at $100°$ C. and, after cooling, poured into about 0.5 litre of ice water. This is extracted four times with methylene chloride and the combined extraction solutions are evaporated.

121 g of a dark liquid are obtained which contains 56.2% by weight of 2-chloro-5-benzyl-pyridine and 29.7% by weight of benzyl chloride, according to gas chromatographic analysis. 32 g of a colourless oil (content: 95.6% of 2-chloro-5-benzyl-pyridine) of boiling point $132°-134°$ C./1 mbar are obtained by vacuum distillation, corresponding to a yield of 34% of theory over the last two stages (Examples (II-2) and 2), starting from 97.2 g (0.465 mol) of the compound III-2 on the occasion.

The compounds of the formula (I) listed in Table 1 below for example may also be prepared in analogy to Examples 1 and 2 and in accordance with the general description of the process according to the invention.

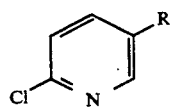
(I)

Table 1: Examples of compounds of the formula (I) to be prepared according to the invention

| Ex. No. | R | Boiling point | Yield over last 2 stages |
|---|---|---|---|
| 3 | $C_2H_5$ | 95° C.–100° C. (at 12 mbar) | 49% |
| 4 | $C_5H_{11}$ | | 12% |

Example 5

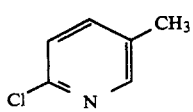

13.3 g (0.105 mol) of oxalyl chloride are added dropwise at an internal temperature of 0° C. to +5° C. to 40.9 g (0.56 mol) of dimethylformamide over the course of 40 minutes. 6.6 g of N-benzyl-N-(1-propenyl)-acetamide (crude product from Example (II-1)) are then added dropwise at the same temperature. The reaction mixture is then stirred for 12 hours at 100° C. and, after cooling, poured into 140 g of ice water. This is extracted four times with methylene chloride and the combined extraction solutions are evaporated.

10.9 g of a brown-yellow liquid residue which contains 28.2% 2-chloro-5-methyl-pyridine, according to gas chromatographic analysis, are obtained. Relative to the purity of the starting material (content: 73% of (II)), this therefore gives a yield of 93% of theory.

Example 6

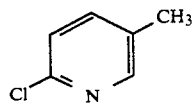

First, 10.4 g (0.105 mol) of phosgene and 40.9 g (0.56 mol) of dimethylformamide are reacted at 0° C. to +5° C. 6.6 g of N-benzyl-N-(1-propenyl)-acetamide (crude product from Example (II-1)) are then added dropwise. The reaction mixture is then stirred for 12 hours at 100° C. and subsequently worked up as described in Example 5.

2-Chloro-5-methyl-pyridine is obtained in a yield of 92% of theory in this way.

Starting materials of the formula (II)

Example (II-1)

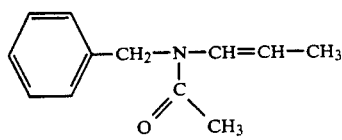

68.4 g (0.465 mol) of N-propylidene-benzylamine (see Example (III-1) are dissolved in 250 ml of toluene. This solution is cooled to about 5° C. and 47.1 g (0.465 mol) of triethylamine and 47.4 g (0.465 mol) of acetic anhydride are added dropwise at this temperature, one after the other, each over the course of 30 minutes. The reaction mixture is subsequently stirred for about 3 hours more at 20° C. The more highly volatile components are then distilled off at 50° C./2 mbar.

13.7 g of a yellow, oily residue, which consists in the main of N-benzyl-N-(1-propenyl)-acetamide, are obtained and this is used without further purification in the next stage (see Example 1). The product may be purified by vacuum distillation (boiling range: 120° C.–130° C./1 mbar) and subsequent column chromatography (silica gel; petroleum ether/ethyl acetate, 2:1).

The compounds of the formula (II) listed in Table 2 below may also for example be prepared in analogy to Example (II-1).

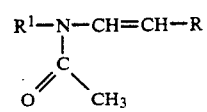
(II)

TABLE 2

Examples of compounds of the formula (II)

| Ex. No. | R | $R^1$ | Physical data |
|---|---|---|---|
| II-2 | $CH_2$—⌬ | $CH_2$—⌬ | $n_D^{20}$: 1.5503 |
| II-3 | $C_2H_5$ | $CH_2$—⌬ | |
| II-4 | $C_5H_{11}$ | $CH_2$—⌬ | |
| II-5 | $CF_3$ | $CH_2$—⌬ | |
| II-6 | $C_3H_7$ | $CH_2$—⌬ | |
| II-7 | $CH_3$ | $n-C_3H_7$ | b.p. = 92–96° C./ 14 mm |
| II-8 | $CH_3$ | $n-C_4H_9$ | b.p. = 113–115° C./ 16 mm |
| II-9 | $CH_3$ | $t-C_4H_9$ | b.p. = 116–122° C./ 14 mm |

Precursors of the formula (III)

Example III-1

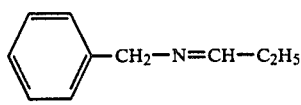

53.5 g (O.,j mol) of benzylamine are cooled to 5° C. and treated dropwise, while stirring, with 29 g (0.5 mol) of propionaldehyde. The mixture is allowed to reach room temperature and 15 g of potassium hydroxide (pellets) are added to it. The lower (aqueous) phase is then separated off, and the organic phase is treated with a further 5 g of potassium hydroxide and left to stand overnight.

Decantation gives 68.6 g (93% of theory) of N-propylidenebenzylamine as a clear liquid which cannot be distilled without decomposing, and is therefore reacted further directly (see Example (II-1)).

The compounds of the formula (III) listed in Table 3 below may also for example be prepared in analogy to Example (III-1).

TABLE 3

$R^1-N=CH-CH_2-R$ (III)
Examples of compounds of formula (III)

| Ex. No. | R | $R^1$ | Physical data |
|---|---|---|---|
| III-2 | 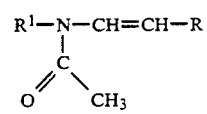 | | $n_D^{20}$: 1.5802 |
| III-3 | $C_2H_5$ | | |
| III-4 | $C_3H_7$ | | |
| III-5 | $C_5H_{11}$ | | |
| III-6 | $CF_3$ | | |
| III-7 | $C_4H_9$ | 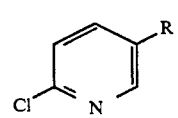 | |
| III-8 | $CH_3$ | $n-C_3H_7$ | b.p. = 101° C. |
| III-9 | $CH_3$ | $n-C_4H_9$ | b.p. = 118-127° C. |
| III-10 | $CH_3$ | $t-C_4H_9$ | |

I claim:

1. A process for the preparation of a 5-substituted 2-chloropyridine of the formula $$\text{(I)}$$

in which
R is optionally halogen-substituted alkyl or arylalkyl, which comprises combining about 1 to 10 moles of a chlorinating agent selected from the group consisting of phosphoryl chloride, phosgene and oxalylchloride with at least an equal molar amount from about 1 to 20 moles of dimethylformamide at a temperature of about 0° to 20° C., adding thereto about one molar amount of an acetenamide of the formula $$R^1-N-CH=CH-R \quad \text{(II)}$$
$$\underset{O}{\overset{|}{C}}\diagdown CH_3$$

in which
R' is optionally halogen-substituted alkyl or arylalkyl, and maintaining the mixture for a period of time at about 80° to 120° C.

2. A process according to claim 1, in which R is optionally fluorine- or chlorine-substituted $C_1-C_6$-alkyl or phenyl-$C_1-C_2$-alkyl.

3. A process according to claim 1, in which R is methyl, ethyl or benzyl.

4. A process according to claim 1, in which about 1.5 to 5 moles of the chlorinating agent are employed per 2 to 15 moles of dimethylformamide.

5. A process according to claim 1, in which the chlorinating agent comprises phosgene.

6. A process according to claim 1, in which the chlorinating agent comprises oxalylchloride.

* * * * *